(12) United States Patent
Veasey et al.

(10) Patent No.: US 8,939,945 B2
(45) Date of Patent: Jan. 27, 2015

(54) DRIVE MECHANISM FOR A DRUG DELIVERY DEVICE

(75) Inventors: Robert Veasey, Leamington Spa (GB); David Plumptre, Droitwich Spa (GB); Christopher Jones, Tewkesbury (GB); Garen Kouyoumjian, Leamington Spa (GB); Catherine Anne MacDonald, Ashby-de-la-Zouch (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 273 days.

(21) Appl. No.: 13/497,769

(22) PCT Filed: Sep. 29, 2010

(86) PCT No.: PCT/EP2010/064425
§ 371 (c)(1),
(2), (4) Date: Aug. 3, 2012

(87) PCT Pub. No.: WO2011/039232
PCT Pub. Date: Apr. 7, 2011

(65) Prior Publication Data
US 2012/0296287 A1 Nov. 22, 2012

(30) Foreign Application Priority Data
Sep. 30, 2009 (EP) ..................... 09171765

(51) Int. Cl.
*A61M 5/00* (2006.01)
*A61M 5/315* (2006.01)
*A61M 5/24* (2006.01)

(52) U.S. Cl.
CPC ....... *A61M 5/31511* (2013.01); *A61M 5/31555* (2013.01); *A61M 5/3156* (2013.01); *A61M 5/31585* (2013.01); *A61M 5/24* (2013.01); *A61M 5/31505* (2013.01); *A61M 2005/2407* (2013.01)
USPC .......................... 604/211; 604/224

(58) Field of Classification Search
CPC ................. A61M 5/31511; A61M 5/3156
USPC .......................... 604/207–211, 224
See application file for complete search history.

(56) References Cited

U.S. PATENT DOCUMENTS

| 4,659,327 A | 4/1987 | Bennett et al. |
| 2006/0247581 A1 | 11/2006 | Pedersen et al. |

FOREIGN PATENT DOCUMENTS

| CA | 2 687 041 A1 | 12/2008 |
| DE | 10237258 B4 | 9/2006 |
| EP | 0338806 A2 | 10/1989 |
| EP | 1074273 A1 | 2/2001 |
| JP | 6-190040 A | 7/1994 |
| JP | 2010-527665 A | 8/2010 |

OTHER PUBLICATIONS

Form PCT/IB/326, Notification Concerning Transmittal of International Preliminary Report on Patentability.

*Primary Examiner* — Theodore Stigell
*Assistant Examiner* — Benjamin Koo
(74) *Attorney, Agent, or Firm* — McDonnell Boehnen Hulbert & Berghoff LLP

(57) ABSTRACT

A lead screw (5) with a screw thread (6) is arranged in a body (1) along an axis (4) and coupled to a lead screw nut (7) with a drive feature (8), so that the lead screw is helically rotatable in the lead screw nut. The lead screw and the lead screw nut are provided with stop features (9) interfering with a rotation of the lead screw in the lead screw nut when a force is applied to the lead screw in an axial direction. The lead screw nut has a surface area facing a guide feature (10) of the body. This surface area has a slope (12) varying around the axis. The assembly interacts such that the lead screw nut rotates in one rotational direction when a force is applied to the lead screw in the axial direction.

15 Claims, 4 Drawing Sheets

DRIVE MECHANISM FOR A DRUG DELIVERY DEVICE

CROSS REFERENCE TO RELATED APPLICATIONS

The present application is a 35 U.S.C. 371 National Application of PCT/EP2010/064425 filed Sep. 29, 2010, which claims priority to European Patent Application No. 09171765.2, filed Sep. 30, 2009, the entire contents of which are incorporated entirely herein by reference.

The present invention relates to a drive mechanism for a drug delivery device, especially for a device that is designed for the delivery of fixed doses.

Portable drug delivery devices are used for the administration of a drug that is suitable for self-administration by a patient. A drug delivery device is especially useful in the shape of a pen, which can be handled easily and kept everywhere available.

A type of drug delivery device is constructed to be refillable and reusable many times. A drug is delivered by means of a drive mechanism, which may also serve to set the dose or amount to be delivered.

DE 102 37 258 B4 describes a drug delivery device in the shape of an injection pen having a drive mechanism, which allows to deliver a plurality of different prescribed doses. The drive mechanism comprises elements which are rotated relatively to one another around a common axis. They are coupled by unidirectional gears.

It is an object of the present invention to disclose a new drive mechanism for a drug delivery device.

This object is achieved by a drive mechanism according to claim 1. Further objects are achieved by variants and embodiments according to the dependent claims.

The drive mechanism for a drug delivery device comprises a body with a distal end and a proximal end, which are spaced apart in the direction of an axis. A lead screw and a lead screw nut are arranged within the body. The lead screw is arranged along the axis and movable relatively to the body. The lead screw and the lead screw nut are provided with a screw thread and a drive feature coupling the lead screw and the lead screw nut, so that the lead screw is helically rotatable in the lead screw nut. The lead screw and the lead screw nut are provided with stop features interfering with a rotation of the lead screw and the lead screw nut relative to one another when a force is applied to the lead screw in the proximal direction.

The body has a guide feature restricting a movement of the lead screw nut, and the lead screw nut has a surface area facing the guide feature. This surface area of the lead screw nut has a slope varying around the axis. The screw thread, the slope, and the guide feature interact in such a manner that the lead screw nut rotates in one rotational direction when a force is applied to the lead screw in the proximal direction.

The body can be any housing or any component that forms part of a housing, for example. The body can also be some kind of an insert connected with an exterior housing. The body may be designed to enable the safe, correct, and/or easy handling of the device and/or to protect it from harmful liquids, dust or dirt. The body can be unitary or a multipart component of tubular or non-tubular shape. The body may house a cartridge, from which doses of a drug can be dispensed. The body can especially have the shape of an injection pen.

The term "distal end" refers to a part of the body or housing which is intended to be arranged at a portion of the drug delivery device from which a drug is dispensed. The term "proximal end" refers to a part of the body or housing which is remote from the distal end. The term "distal direction" refers to a movement in the same direction as a movement from the proximal end towards the distal end, not specifying a point of departure nor an end point, so that the movement may go beyond the distal end. The term "proximal direction" refers to a movement in the direction opposite to the distal direction.

The term "lead screw" encompasses any element, whether unitary or of multipart construction, that is provided to transfer a movement to a piston, thus working as a piston rod, especially for the purpose of dispensing a drug. The lead screw may be flexible or not.

The drive mechanism can be used to expel a drug from a receptacle or cartridge inserted in the body of a drug delivery device. The drug delivery device can be a disposable or reusable device designed to dispense a dose of a drug, especially a liquid, which may be insulin, a growth hormone, a heparin, or an analogue and/or a derivative thereof, for example. The drug may be administered by a needle, or the device may be needle-free. The device may be further designed to monitor physiological properties like blood glucose levels, for example. Each time the lead screw is shifted in the distal direction with respect to the body, a certain amount of the drug is expelled from the drug delivery device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In an embodiment of the drive mechanism, the slope of the surface area interacting with the guide feature generates a rotation of the lead screw nut with respect to the body, irrespective of the stop features interfering with the rotation. The rotational direction of the lead screw nut is the same as the rotational direction of the lead screw with respect to the body.

In a further embodiment, the lead screw nut is rotationally locked to the body during a movement of the lead screw in the distal direction and is not rotationally locked to the body during a movement of the lead screw in the proximal direction.

In a further embodiment, the lead screw is provided with the screw thread and has a further screw thread, the screw thread and the further screw thread having opposite senses of rotation. The lead screw is guided by the lead screw nut being engaged with the screw thread of the lead screw; and a drive member can be coupled with the lead screw by means of the further screw thread of the lead screw.

In a further embodiment, the drive member and the lead screw are coupled by means of a further screw thread that can be overridden.

In a further embodiment, the stop features comprise contact faces perpendicular to the lead screw access.

In a further embodiment, the screw thread is a helical groove, and the stop features comprise recesses in the groove, the recesses extending in the distal direction.

In a further embodiment, a recess of the screw thread is provided to inhibit a helical movement of the lead screw when an axial force is exerted on the lead screw towards the proximal end.

In a further embodiment, a recess of the screw thread is limited in the distal direction by a flat surface that is orthogonal to the axis.

In a further embodiment, the helical groove forming the screw thread has a sidewall facing the distal end and a slope measured by an angle between a tangent to a helix formed by the screw thread and a plane that is orthogonal to the axis. The sidewall has a corresponding slope, which vanishes in each of the recesses.

A further embodiment comprises a removable and attachable part of the body comprising a receptacle provided for a cartridge containing a drug. A coupling feature of the body and a corresponding coupling feature of the lead screw nut are provided to lock the lead screw nut rotationally to the body when the part comprising the receptacle is attached. The lead screw nut is able to rotate relatively to the body when the part comprising the receptacle is removed.

In a further embodiment, the lead screw nut rotates relatively to the body when the lead screw is reset in the proximal direction after the part comprising the receptacle has been removed.

In a further embodiment, a drive member is coupled to the lead screw in such a manner that the drive member can be shifted in the proximal direction without rotating the drive member with respect to the body and without changing the relative position of the lead screw with respect to the body.

In a further embodiment, the drive member is a substantially cylindrical drive sleeve, and the lead screw enters the drive sleeve.

In a further embodiment, a piston that is provided to expel a drug is driven in the distal direction by the lead screw.

An embodiment of the drive mechanism and its operation are described in the following as an example. During a delivery operation, the lead screw is helically moved in the distal direction with respect to the body. The lead screw is guided by the lead screw nut being engaged with the screw thread of the lead screw. The drive feature of the lead screw nut can be a protruding element, a recess or a segment of a screw thread. The stop features interfering with the rotation of the lead screw are arranged such that the distal movement of the lead screw during the dispense operation is not inhibited.

The stop features are provided to enable a set operation, by which a fixed dose that is to be dispensed can be preset. For this purpose, a drive member, which can especially be a drive sleeve surrounding the lead screw, is drawn in the proximal direction relatively to the body and to the lead screw. The drive member is coupled with the lead screw. The coupling can be achieved by a feature providing an engagement between the drive member and the lead screw, particularly by a further screw thread of the lead screw, for example. During the set operation, the lead screw must not be moved. Therefore, the engagement between the drive member and the lead screw is temporarily released during the set operation. The feature providing the engagement between the drive member and the lead screw is overridden by the movement of the drive member in the proximal direction. In spite of the engagement between the drive member and the lead screw, the drive member can therefore be moved without being rotated, while the lead screw stays stationary with respect to the body. Overriding the engagement between the drive member and the lead screw may be further facilitated if the engaging means is formed by confined features like protruding elements, plugs or spikes.

After the drive member has been moved a distance corresponding to a dimension of the feature providing the engagement between the drive member and the lead screw, the pitch of a screw thread, for example, the drive member and the lead screw reengage, and the user can advance the lead screw by pushing the drive member back in the distal direction. This method of operation by disengaging and reengaging the drive member with the lead screw relies entirely on the lead screw remaining substantially stationary during the setting operation. Should the lead screw rotate or move axially during setting, then the drive member would very likely not correctly reengage with the lead screw and thus cause dose inaccuracy. Therefore, the lead screw nut guiding the helical movement of the lead screw with respect to the body is rotationally locked to the body during the dispense operation and, furthermore, the lead screw and the lead screw nut are provided with stop features interfering with the rotation of the lead screw in such a manner that the rotation is inhibited in the positions of the lead screw which are obtained after the drug delivery and before the setting of a new dose. The rotation of the lead screw is thus locked with respect to the lead screw nut, and the lead screw nut is prevented from rotating relatively to the body. Therefore, when the drive member is drawn in the proximal direction, the relative linear motion between the drive member and the lead screw causes the engagement means engaging the drive member with the stationary lead screw to be overridden and thus the engagement between the drive member and the lead screw to be released. The stop features are therefore preferably arranged on the distal sidewall of the screw thread of the lead screw, while the screw thread is smooth, forming a helix, on its proximal sidewall. When the drive member is pushed in the distal direction, the guide means of the lead screw nut engaging the screw thread of the lead screw stays in contact with the smooth proximal sidewall of the screw thread, thus enabling a smooth helical movement of the lead screw sliding through the opening of the lead screw nut. Therefore, the stop features do not interfere with the relative motion of the lead screw with respect to the lead screw nut during the dispense operation.

The drive mechanism allows an easy reset operation, by which the lead screw is returned to its start position near the proximal end of the body. This feature is especially useful in drug delivery devices that are designed to be reusable. A reusable drug delivery device can comprise a body having a receptacle that can be filled with a drug. The receptacle can be provided for a cartridge containing the drug. To exchange the cartridge, a removable and attachable part of the body is removed, the empty cartridge is removed and a new full cartridge is inserted. The lead screw is used to drive a piston expelling the drug from the cartridge through a nozzle or needle that is attached to the body at its distal end, for example. The lead screw is shifted in the proximal direction, before a new cartridge can be inserted. In order to facilitate the reset operation, the lead screw nut is disengaged from the body and is free to rotate relatively to the body. The lead screw can then be shifted in the proximal direction relatively to the drive member while the lead screw and the drive member stay coupled by the engaging means. The lead screw is just rotated in the appropriate way to enable the relative movement with respect to the drive member, without the engaging means having to be overridden. The lead screw nut rotates with respect to the lead screw to enable the movement of the lead screw. The lead screw nut can thus be held at its axial position with respect to the body, and the lead screw nut need not be shifted relatively to the body.

As the lead screw is pushed in the proximal direction, the stop features acting between the lead screw and the lead screw nut are apt to engage according to the relative rotation of the lead screw and the lead screw nut. Because the stop features are provided to interfere with this relative rotation during the set operation, the reset operation is adversely affected by the stop features interrupting the rotation. The lead screw nut is therefore formed such that means are provided which disengage the stop features during the reset operation. To this end, a surface area of the lead screw nut is provided with a slope varying in the azimuthal direction along the circumference of the lead screw nut. This surface area is arranged opposite to the guide feature of the body, so that the guide feature slides on the sloping surface area of the lead screw nut. When an axial force is exerted on the lead screw in the proximal direction, the slope of the lead screw nut and the guide feature of the body interact in such a manner that the stop features do not stop the rotation.

The stop features can especially be provided by recesses of a helical groove forming the screw thread of the lead screw. The recesses can have contact faces arranged perpendicular to the axis and interrupting the smooth helix of the relevant sidewall of the groove forming the screw thread. The drive feature of the lead screw nut is formed in such a manner that it enters the recesses and stops on the contact face. The slope of the surface area of the lead screw nut sliding on the guide feature of the body then generates a further rotation of the lead screw nut. Because the section of the slope that is in contact with the guide feature of the body is alternatingly ascending and descending during a rotation of the lead screw nut with respect to the body, the lead screw nut performs a reciprocating motion in the axial direction and is alternatingly driven by the descending slope or rotated against the effect of the ascending slope by means of the drive feature being guided by the screw thread of the lead screw.

In the following, a more detailed description of examples and embodiments of the drive mechanism is given in conjunction with the appended figures.

Figure 1:
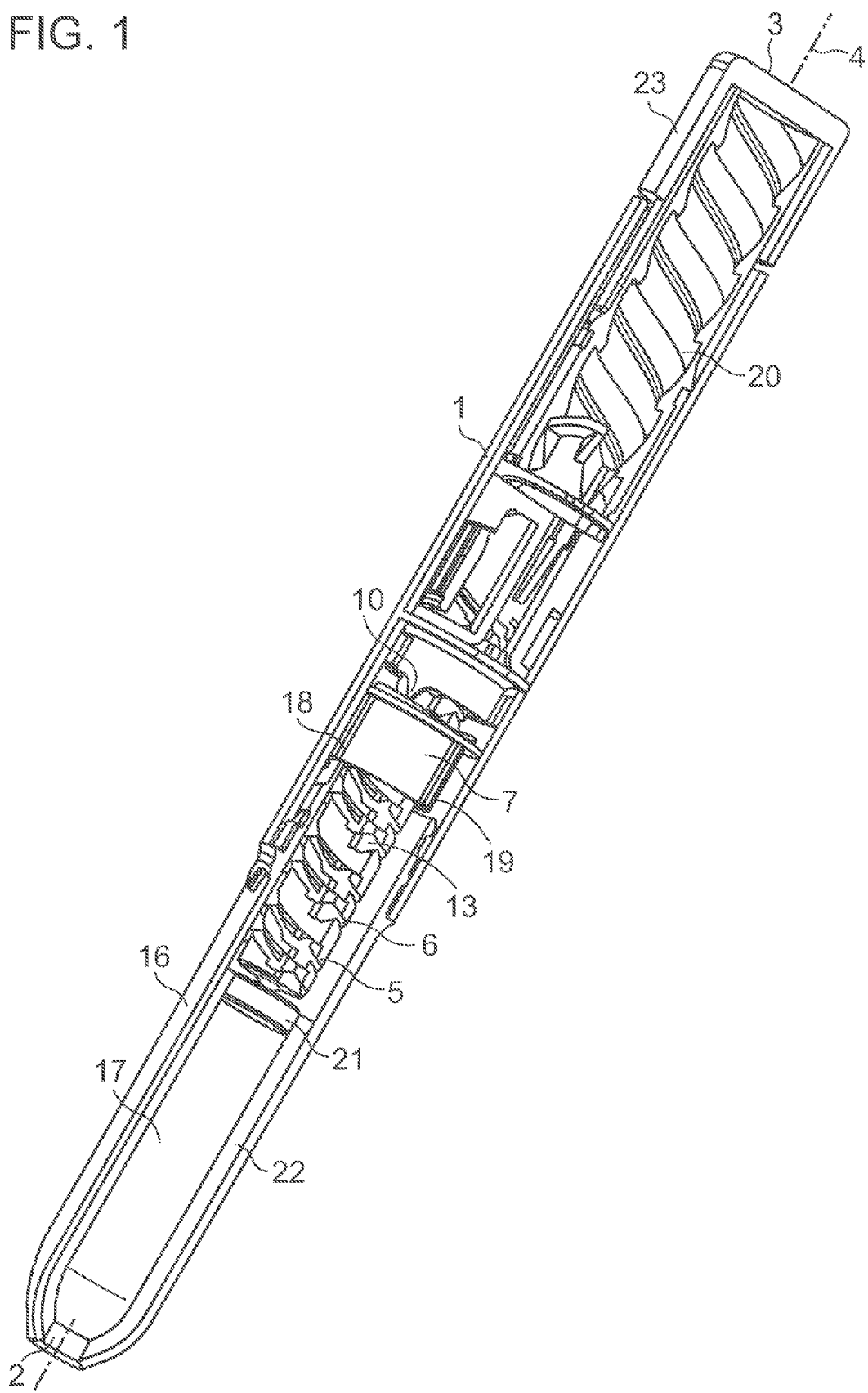
FIG. 1 shows a perspective view of a cross-section of an injection pen comprising an embodiment of the drive mechanism.

FIG. 1 shows a cut-away view of an injection pen comprising the drive mechanism. The drive mechanism is arranged in a body 1 having a distal end 2 and a proximal end 3. The lead screw 5 is arranged along an axis 4 of the device. The screw thread 6 of the lead screw 5 is coupled to a drive feature of the lead screw nut 7 engaging the screw thread 6, in order to guide a helical movement of the lead screw 5 with respect to the lead screw nut 7. In further embodiments, the screw thread and the drive feature can be reversed such that the lead screw is provided with discrete drive features and the lead screw nut is provided with a helical screw thread.

The embodiment shown in FIG. 1 comprises a drive member 20, which can be operated by the user by means of a button 23, which is arranged at the proximal end 3 and juts out of the body 1. The drive member 20 is coupled or engaged with the lead screw 5. This is achieved, in this embodiment, by means of a further screw thread 13 of the lead screw 5. The drive member 20 can especially be a drive sleeve of essentially cylindrical shape, the axis of the drive sleeve being arranged parallel to the axis 4 of the device. The lead screw 5 may be disposed to enter the drive member 20.

The lead screw nut 7 is rotationally locked to the body 1 by means of a coupling feature 18 of the body 1 and a corresponding coupling feature 19 of the lead screw nut 7. The removable and attachable part 16 of the body 1 is provided as a cartridge holder. When this part 16 is removed from the rest of the body 1, a cartridge 22 can be inserted in a receptacle 17 inside this part 16. Then, the part 16 is attached to the body 1, so that the lead screw 5 is brought into contact with a piston 21. The piston 21 is provided to expel a drug from the volume of the receptacle 17 and can particularly be arranged within the cartridge 22. A bearing can be arranged between the lead screw 5 and the piston 21 in order to prevent any damage that might be caused by a relative movement between the lead screw 5 and the piston 21. The lead screw 5 functions as a piston rod to advance the piston 21 in the distal direction.

The screw thread 6 serves to guide the movement of the lead screw 5 helical with respect to the body 1. The coupling feature 18 of the body 1, which locks the lead screw nut 7 rotationally to the body 1, is preferably attached to or formed by a part of the removable and attachable part 16. This enables the user to release the lead screw nut 7 from its rotational coupling to the body 1 by removing the removable and attachable part 16. This makes the reset operation possible, which is described below.

A set operation is performed by pulling the drive member 20 out of the body 1 in the proximal direction. When the drive member 20 is thus pulled in the proximal direction, it exerts an axial load on the lead screw 5. To prevent the lead screw 5 from performing a helical movement through the lead screw nut 7 in the proximal direction, yielding to the axial load, stop features are provided on the screw thread 6. The stop features can be designed in various shapes, and an embodiment will be described in detail to give an example. The stop features may be formed by recesses in the distal sidewall of the screw thread 6, the surfaces of the recesses preferably having flat portions that are arranged essentially perpendicular to the axis 4. When the drive feature of the lead screw nut 7 comes into contact with one of the flat portions, the generally perpendicular orientation of the flat portion with respect to the axis 4 causes the guidance of the helical movement of the lead screw 5 with respect to the body 1 to be stopped. It is favorable if the drive feature of the lead screw nut 7 that engages with the screw thread 6 of the lead screw 5 and is stopped in the recesses is made up of one or more individual drive features and is not formed by a completely continuous helix. The stop features are arranged in such a fashion that, after a dose of the drug has been fully delivered and the device is ready for the next dose to be set, one of the stop features is in a position ready to stop the rotation of the lead screw 5 when the drive member 20 is pulled in the proximal direction. The axial load exerted on the lead screw 5 is then compensated by the drive feature of the lead screw nut 7 being held stationary by the relevant stop feature, particularly by the flat portion of the relevant recess. This acts to lock the rotation of the lead screw 5 rather than rotate it, because the lead screw nut 7 is rotationally locked to the body 1 during the operations of setting and dispensing a dose. Essentially, the flat surfaces on the screw thread 6 are designed to prevent a back-driving of the lead screw 5 during a set operation. The lead screw 5 can therefore be moved only in the distal direction as long as the removable and attachable part 16 stays attached to the body 1 and the lead screw nut 7 is rotationally locked to the body 1.

The lead screw 5 is allowed to be reset in the proximal direction by making the lead screw nut 7 rotate freely with respect to the lead screw 5. The lead screw nut 7 is locked in rotation with respect to the body 1 during setting and dispensing. The locking and releasing of the lead screw nut 7 is preferably controlled by the removable and attachable part 16, which can be a cartridge holder in particular. The suitable rotation of the lead screw nut 7 is maintained by the special shape of the lead screw nut 7 in conjunction with the action of the guide feature 10 of the body 1.

Figure 2:
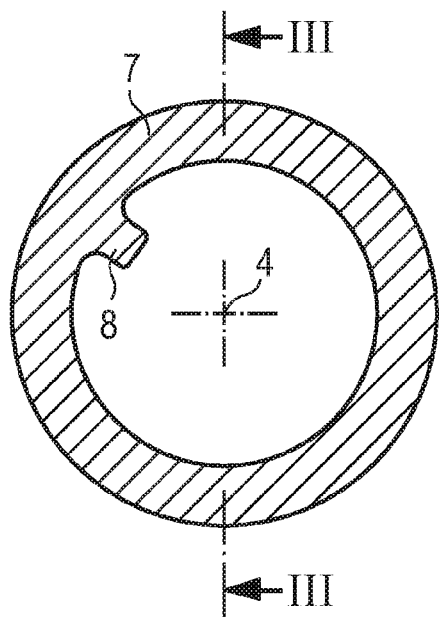
FIG. 2 shows a cross-section of the lead screw nut transverse to the axis.

FIG. 2 shows a cross-section of the lead screw nut 7 transverse to the axis 4. The lead screw nut 7 comprises a central opening with a protruding element forming the drive feature 8. The cross-section indicated in FIG. 2 is shown in FIG. 3.

Figure 3:
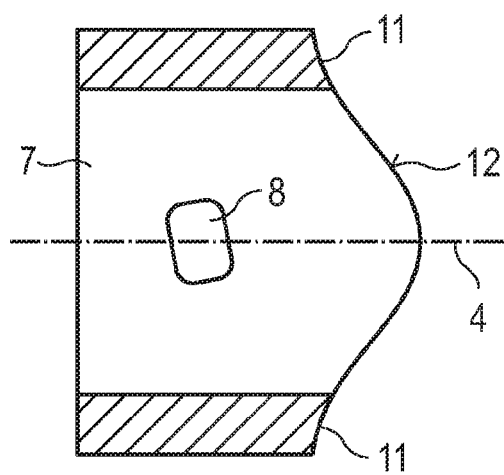
FIG. 3 shows the cross-section of the lead screw nut indicated in FIG. 2.

FIG. 3 shows a cross-section of the lead screw nut 7, the axis 4 lying in the plane of the cross-section. The drive feature 8 is shown to be arranged on the inner sidewall of the central opening of the lead screw nut 7. The surface area 11 facing the guide feature 10 of the body 1 is shown to have a slope 12, which is alternatingly ascending and descending around the circumference of the lead screw nut 7. The interaction of the screw thread 6, the slope 12 and the guide feature 10 of the body 1 is described in the following in conjunction with FIGS. 4 and 5.

Figure 4:
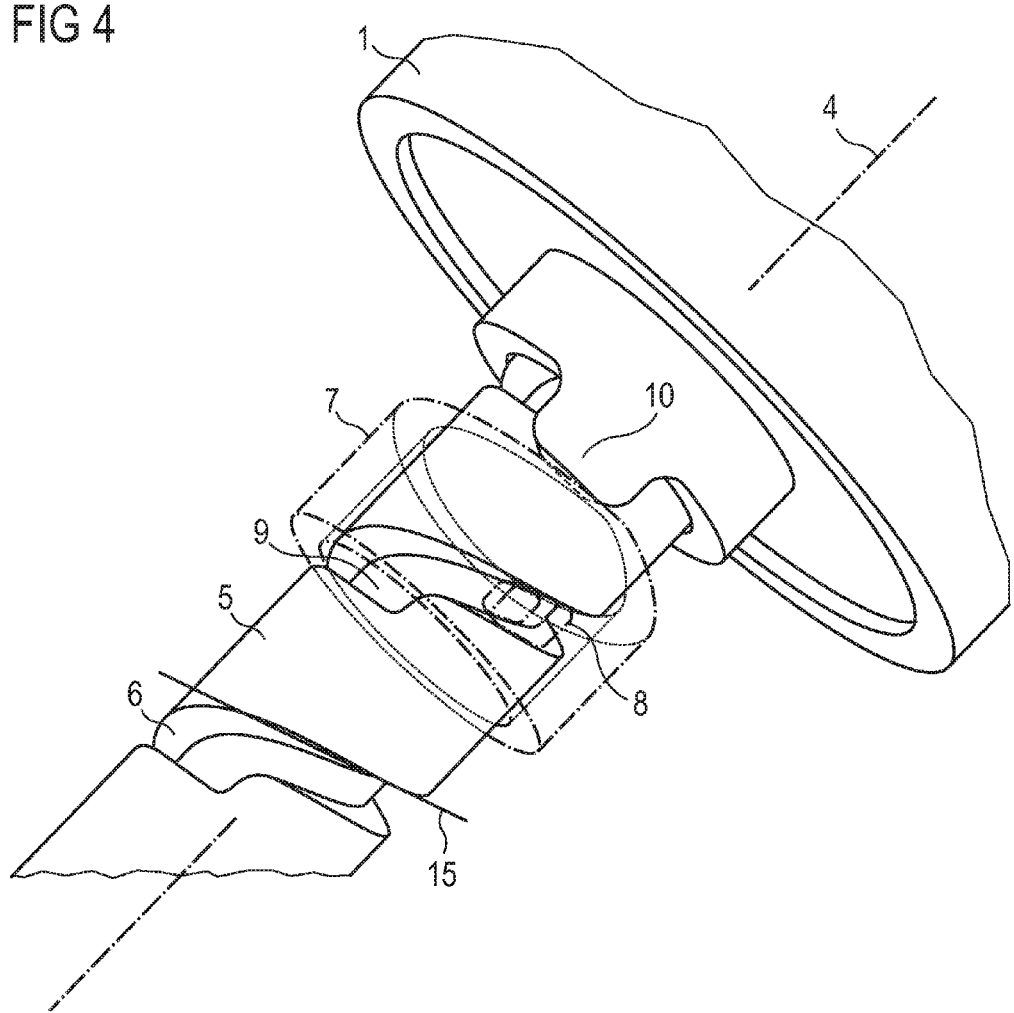
FIG. 4 shows the arrangement of the lead screw, the lead screw nut and the guide feature of the body during the rotation of the lead screw nut.

FIG. 4 shows the arrangement of the lead screw 5, the lead screw nut 7 and the guide feature 10 of the body 1 in the region of the lead screw nut 7. The lead screw nut 7 is shown transparent, the broken and dotted lines indicating the contours that could also be seen in the same perspective view onto an opaque lead screw nut, while the dotted lines are the hidden contours, which are behind the lead screw 5 or belong to the central opening of the lead screw nut 7. The lead screw 5 is provided with the screw thread 6, which is formed by a helical groove in this embodiment. The slope 15 of the screw thread 6 can be measured by the angle between a tangent to a helix formed by the screw thread 6 and a plane that is orthogonal to the axis 4, as indicated by the straight line in the direction of the slope 15 in FIG. 4. During a reset operation, the lead screw 5 is pushed in the proximal direction, which is the direction to the right upper side in FIG. 4. This means that the drive feature 8 of the lead screw nut 7 is held in contact with the distal sidewall of the screw thread 6. When the lead screw 5 is shifted in the proximal direction, a rotation of the lead screw nut 7 with respect to the lead screw 5 is maintained as long as the drive feature 8 of the lead screw nut 7 is guided by the helix of the screw thread 6.

Figure 5:
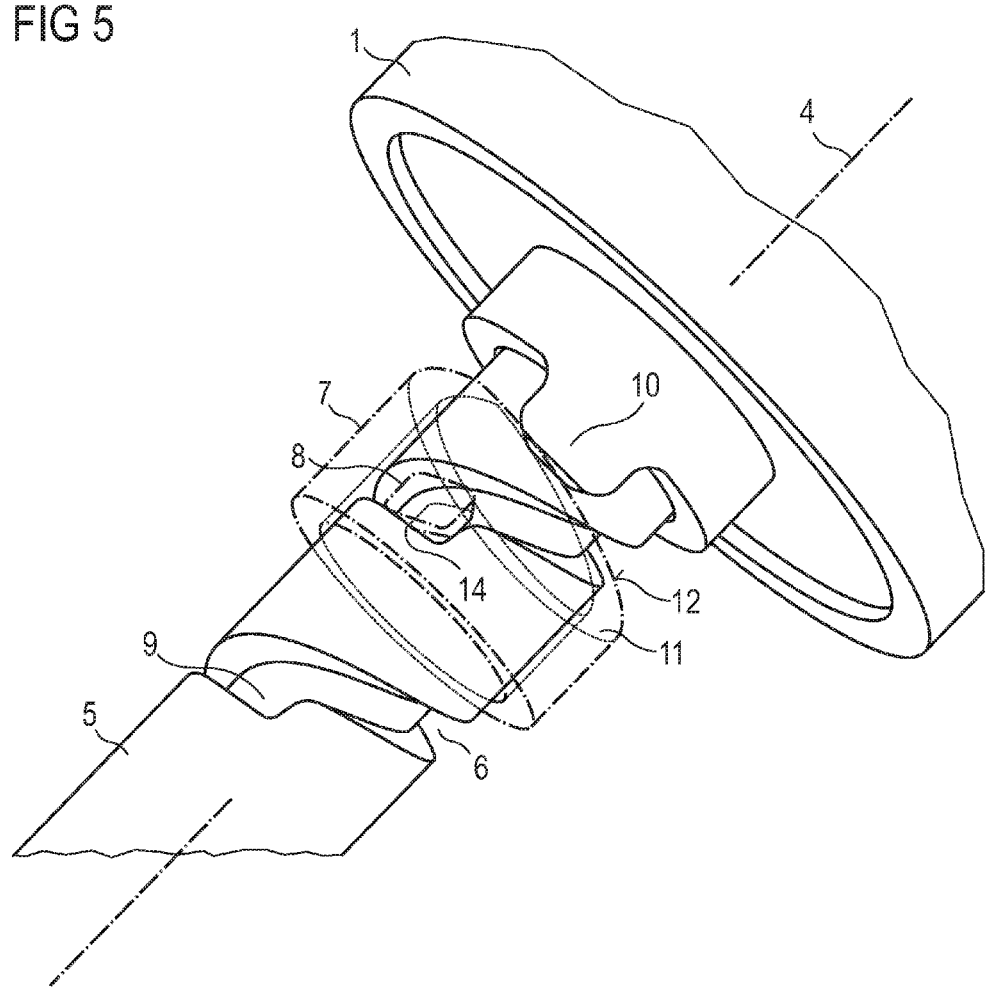
FIG. 5 shows the arrangement according to FIG. 4 when the drive feature of the lead screw nut engages the stop feature.

FIG. 5 shows the arrangement according to FIG. 4 in a position of the lead screw nut 7 in which the drive feature 8 of the lead screw nut 7 is captured in one of the stop features 9. In this embodiment, the stop features 9 are formed by recesses extending in the distal direction and interrupting the helix of the distal sidewall of the screw thread 6. The recesses can be provided with contact faces 14 which are essentially perpendicular to the axis 4, corresponding to the flat portions mentioned above. This means that the slope 15 of the screw thread 6 vanishes in the area of the contact faces 14, where the drive feature 8 of the lead screw nut 7 is consequently not driven further in a rotational movement relative to the lead screw 5. This is the very position that is obtained by the drive feature 8 after the dispense operation and immediately before a new set operation. This position of the lead screw nut 7 with the drive feature 8 engaging the stop feature 9 enables the user to exert an axial load on the lead screw 5 by pulling the drive member 20 in the proximal direction, without making the lead screw 5 rotate. The lead screw 5 cannot rotate because the rotational movement is locked by the drive feature 8 being captured in the recess of the screw thread 6.

During the reset operation, an appropriate rotation of the lead screw nut 7 is generated by the interaction of the slope 12 of the marginal surface area 11 of the lead screw nut 7 and the guide feature 10 of the body 1. When the lead screw 5 is shifted in the proximal direction, the lead screw nut 7 is pressed in the proximal direction so that the guide feature 10 is in contact with said surface area 11. The slope 12 of the surface area 11 is then descending with respect to the direction in which the zone of the surface area 11 that is at a given moment in contact with the guide feature 10 moves during the desired rotation of the lead screw 7. The axial load on a lead screw nut 7 in the proximal direction will therefore cause the guide feature 10 to drive the lead screw nut 7 in the direction of the desired rotation. The rotation of the lead screw nut 7 is therefore maintained each time the stop features 9 are apt to interfere with the rotation.

FIG. 4 shows the position of the lead screw nut 7 after the drive feature 8 has been driven out of the recess of the stop feature 9. In this position, the guide feature 10 of the body 1 is in contact with the ascending slope of the surface area 11 facing the guide feature 10. The ascending section of the slope 12 of the surface area 11 of the lead screw nut 7 and the slope 15 of the helix of the screw thread 6 are adapted so that the guidance of the drive feature 8 in the screw thread 6 generates the desired rotation of the lead screw nut 7 even when the ascending slope 12 tends to generate a rotation of the lead screw nut 7 in the opposite direction. The effect of the slope 15 of the screw thread 6 of the lead screw 5 thus prevails over the effect of the guide feature 10 acting on the ascending slope 12 of the lead screw nut 7.

The drive mechanism has a mechanical advantage with high efficiency and may be designed to provide audible, visual and/or tactile feedback both on setting and delivering of each dose. It has low part count, which makes it especially attractive for cost-sensitive device applications. The drive mechanism can be used in a wide range of reusable devices like pen injectors, particularly fixed-dose pen injectors. It is favorably applicable, although not limited, to drug delivery devices provided for the delivery of seven to fourteen doses with every refill.

REFERENCE NUMERALS 1 body
2 distal end
3 proximal end
4 axis
5 lead screw
6 screw thread
7 lead screw nut
8 drive feature of the lead screw nut
9 stop feature
10 guide feature
11 surface area of the lead screw nut 12 slope of the lead screw nut
13 further screw thread
14 contact face
15 slope of the screw thread
16 removable and attachable part of the body
17 receptacle
18 coupling feature of the body
19 coupling feature of the lead screw nut
20 drive member
21 piston
22 cartridge
23 button

The invention claimed is:

1. A drive mechanism for a drug delivery device, comprising:
   a body having a distal end and a proximal end, which are spaced apart in the direction of an axis,
   a lead screw arranged within the body along the axis, the lead screw being movable relatively to the body,
   a lead screw nut,
   the lead screw comprising a screw thread and
   the lead screw nut comprising a drive feature coupling the lead screw and the lead screw nut, so that the lead screw is helically rotatable in the lead screw nut,
   the lead screw comprising a stop features interfering with a rotation of the lead screw and the lead screw nut relative to one another when a force is applied to the lead screw in the proximal direction,
   the body comprising a guide that restricts a movement of the lead screw nut,
   the lead screw nut comprising a surface area facing the guide, the surface area comprising a slope varying around the axis, and
   the screw thread, the slope, and the guide interacting in such a manner that the lead screw nut rotates in a first direction when a force is applied to the lead screw in the proximal direction.

2. The drive mechanism according to claim 1, wherein the slope of the surface area interacting with the guide rotates the lead screw nut in a second direction with respect to the body, irrespective of the stop features interfering with the second direction, the second direction of the lead screw nut being the same as the first direction of the lead screw with respect to the body.

3. The drive mechanism according to claim 1, wherein the lead screw nut is rotationally locked to the body during a movement of the lead screw in the distal direction and is not rotationally locked to the body during a movement of the lead screw in the proximal direction.

4. The drive mechanism according to one of claim 1, wherein the lead screw is provided with the screw thread and with a further screw thread, the screw thread and the further screw thread having opposite senses of rotation.

5. The drive mechanism according to one of claim 1, wherein the stop feature comprises contact faces perpendicular to the lead screw access.

6. The drive mechanism according to one of claim 1, wherein the screw thread comprises a helical groove and the stop feature comprises a recess in the groove extending in the distal direction.

7. The drive mechanism according to claim 6, wherein a recess of the screw thread is provided to inhibit a helical movement of the lead screw when an axial force is exerted on the lead screw in the proximal direction.

8. The drive mechanism according to claim 6, wherein a recess of the screw thread is limited in the distal direction by a flat surface that is orthogonal to the axis.

9. The drive mechanism according to one of claim 6, wherein the helical groove forming the screw thread has a sidewall facing the distal end and a slope measured by an angle between a tangent to a helix formed by the screw thread and a plane that is orthogonal to the axis, and the sidewall has a corresponding slope, which vanishes in each of the recesses.

10. The drive mechanism according to one of claim 1, further comprising:
    a removable and attachable part of the body comprising a receptacle provided for a cartridge containing a drug,
    a coupling feature of the body, and
    a corresponding coupling feature of the lead screw nut,
    the coupling features locking the lead screw nut rotationally to the body when the part comprising the receptacle is attached, and
    the lead screw nut being able to rotate relatively to the body when the part comprising the receptacle is removed.

11. The drive mechanism according to claim 10, wherein the lead screw nut rotates relatively to the body when the lead screw is reset in the proximal direction after the part comprising the receptacle has been removed.

12. The drive mechanism according to one of claim 1, further comprising:
    a drive member coupled to the lead screw in such a manner that the drive member can be shifted in the proximal direction without rotating the drive member with respect to the body and without changing the relative position of the lead screw with respect to the body.

13. The drive mechanism according to claim 12, wherein the drive member is a cylindrical drive sleeve, and the lead screw enters the drive sleeve.

14. The drive mechanism according to claim 12, wherein the drive member and the lead screw are coupled by means of a screw thread that can be overridden.

15. The drive mechanism according to one of claim 1, further comprising:
    a piston that is provided to expel a drug, the piston being driven in the distal direction by the lead screw.

* * * * *